(12) United States Patent
Kamada et al.

(10) Patent No.: US 10,898,088 B2
(45) Date of Patent: Jan. 26, 2021

(54) METHOD AND SYSTEM FOR IMAGE PROCESSING OF INTRAVASCULAR HEMODYNAMICS

(71) Applicant: National University Corporation ASAHIKAWA MEDICAL UNIVERSITY, Asahikawa (JP)

(72) Inventors: Kyosuke Kamada, Asahikawa (JP); Hideaki Hayashi, Tokyo (JP)

(73) Assignee: NATIONAL UNIVERSITY CORPORATION ASAHIKAWA MEDICAL UNIVERSITY, Asahikawa (JP)

( * ) Notice: Subject to any disclaimer, the term of this patent is extended or adjusted under 35 U.S.C. 154(b) by 1128 days.

(21) Appl. No.: 15/023,015

(22) PCT Filed: Sep. 19, 2014

(86) PCT No.: PCT/JP2014/074801
§ 371 (c)(1),
(2) Date: Jun. 1, 2016

(87) PCT Pub. No.: WO2015/041312
PCT Pub. Date: Mar. 26, 2015

(65) Prior Publication Data
US 2016/0262638 A1    Sep. 15, 2016

(30) Foreign Application Priority Data

Sep. 20, 2013 (JP) .................................. 2013-194898

(51) Int. Cl.
*A61B 5/026* (2006.01)
*A61B 5/0275* (2006.01)
(Continued)

(52) U.S. Cl.
CPC .......... *A61B 5/0261* (2013.01); *A61B 5/0035* (2013.01); *A61B 5/0071* (2013.01);
(Continued)

(58) Field of Classification Search
CPC ............ A61B 2505/05; A61B 2576/02; A61B 5/0035; A61B 5/0071; A61B 5/0261;
(Continued)

(56) References Cited

U.S. PATENT DOCUMENTS 5,150,292 A * 9/1992 Hoffmann ............... A61B 6/481
250/303
5,526,817 A * 6/1996 Pfeiffer ................... A61B 5/028
600/481

(Continued)

FOREIGN PATENT DOCUMENTS

| CN | 1494871 A | * 5/2004 | ............ A61B 5/055 |
|---|---|---|---|
| JP | 2010-017396 A | 1/2010 | |
| JP | 2013-003495 A | 1/2013 | |

OTHER PUBLICATIONS

Muir et al. "Quantitative Cerebral Blood Flow Measurements Using MRI." Methods Mol Biol. 2014; 1135: 205-211.*

(Continued)

*Primary Examiner* — Amanda Lauritzen Moher
(74) *Attorney, Agent, or Firm* — Hodgson Russ LLP

(57) ABSTRACT

The disclosure provides technology for analyzing video data of a fluorescent contrast agent shot by a microscope during an operation, and provides a method and system allowing information such as BV, BF and MTT, and vascular wall thickness, to be estimated by fluorescent contrast agent analysis, by applying perfusion analysis methods. The method for processing intravascular hemodynamics images is characterized by shooting video using infrared light, wherein the object of shooting is a portion of a blood vessel (Continued)

injected with a fluorescent contrast agent; performing image analysis of a shape of a chronological change curve of intensity values which are image outputs from the video shooting; and calculating relative data for blood volume and blood flow based on results of the image analysis.

6 Claims, 6 Drawing Sheets

(51) Int. Cl.
| | |
|---|---|
| *A61B 5/00* | (2006.01) |
| *A61B 5/02* | (2006.01) |
| *G06T 7/00* | (2017.01) |
| *A61B 5/0265* | (2006.01) |
| *G01R 33/563* | (2006.01) |
| *A61M 5/00* | (2006.01) |
| *A61B 18/00* | (2006.01) |

(52) U.S. Cl.
CPC ............... *A61B 5/02* (2013.01); *A61B 5/026* (2013.01); *A61B 5/02028* (2013.01); *A61B 5/0263* (2013.01); *A61B 5/0275* (2013.01); *A61B 5/489* (2013.01); *A61B 5/7278* (2013.01); *G06T 7/0012* (2013.01); *A61B 5/0265* (2013.01); *A61B 2018/00404* (2013.01); *A61B 2505/05* (2013.01); *A61B 2576/02* (2013.01); *A61M 5/007* (2013.01); *G01R 33/56366* (2013.01); *G06T 2207/10016* (2013.01); *G06T 2207/10048* (2013.01); *G06T 2207/20221* (2013.01); *G06T 2207/30104* (2013.01)

(58) Field of Classification Search
CPC ... A61B 5/0263; A61B 5/0265; A61B 5/0275; A61B 5/7278; G01R 33/56366; G06T 2207/10016; G06T 2207/10048; G06T 2207/20221; G06T 2207/30104; G06T 7/0012

See application file for complete search history.

(56) References Cited

U.S. PATENT DOCUMENTS

| | | | | |
|---|---|---|---|---|
| 5,865,757 | A * | 2/1999 | Hoeft | A61B 5/0275 600/504 |
| 6,302,850 | B1 * | 10/2001 | Tsukada | A61B 3/1233 600/318 |
| 6,915,154 | B1 | 7/2005 | Docherty et al. | |
| 2002/0183621 | A1 * | 12/2002 | Pfeiffer | A61B 5/0059 600/473 |
| 2007/0112264 | A1 * | 5/2007 | Wu | A61B 5/0263 600/410 |
| 2007/0135716 | A1 * | 6/2007 | Pfeiffer | A61B 5/028 600/481 |
| 2008/0221421 | A1 | 9/2008 | Choi et al. | |
| 2009/0024072 | A1 * | 1/2009 | Criado | A61M 1/3655 604/9 |
| 2010/0041999 | A1 * | 2/2010 | Schuhrke | A61B 5/0261 600/476 |
| 2010/0262017 | A1 * | 10/2010 | Frangioni | A61B 1/0005 600/476 |
| 2011/0028850 | A1 * | 2/2011 | Schuhrke | A61B 5/0261 600/476 |
| 2013/0044126 | A1 | 2/2013 | Yamada | |
| 2015/0112193 | A1 | 4/2015 | Docherty et al. | |

OTHER PUBLICATIONS

Sadek K. Hilal. "Determination of the Blood Flow by a Radiographic Technique." American Journal of Roentgenology.1966; 96(4): 896-906.*

Weichelt, Claudia et al., Quantitative fluorescence angiography for neurosurgical interventions, Biomed Tech, Jun. 2013, vol. 58, No. 3, pp. 269-279.

* cited by examiner

[FIG. 1]
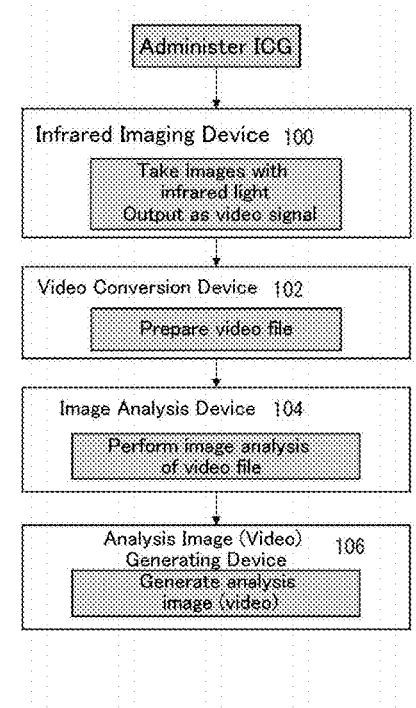
[FIG. 2]
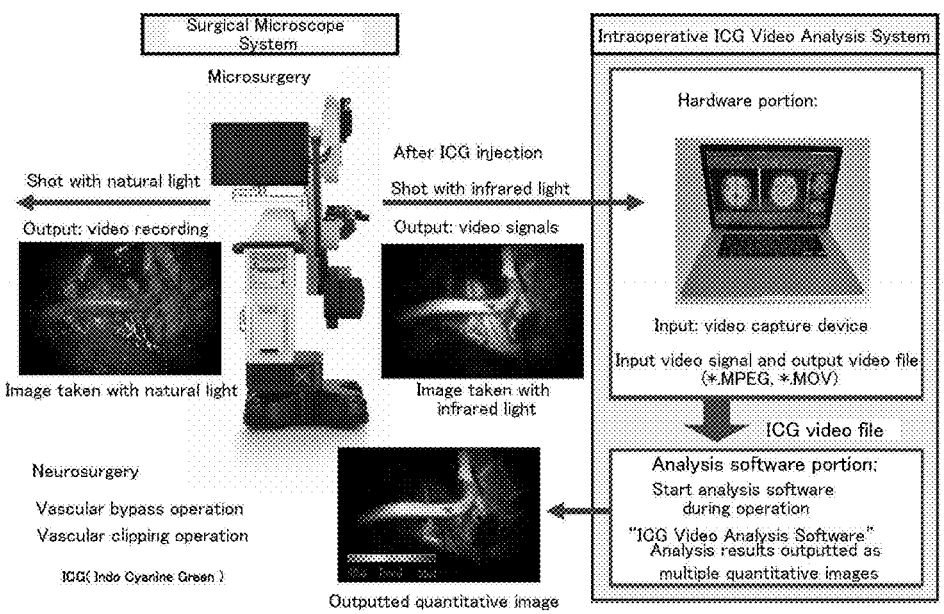

[FIG. 3]
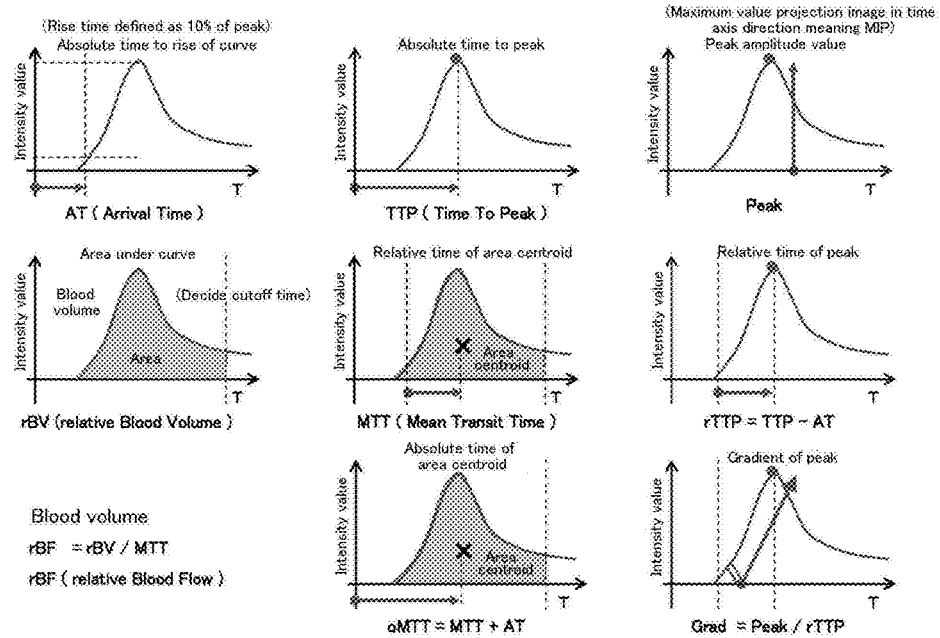
[FIG. 4]
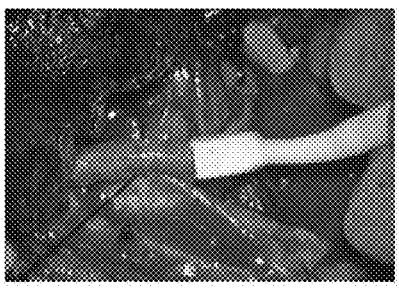
Diagram showing method of measuring quantitative blood flow (eBF) at specific blood vessel positions using electromagnetic blood flow meter
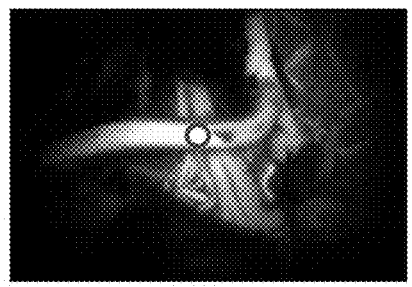
Diagram showing preparation of ROI (circled portion) at same blood vessel position in fluorescent contrast video

[FIG. 5]
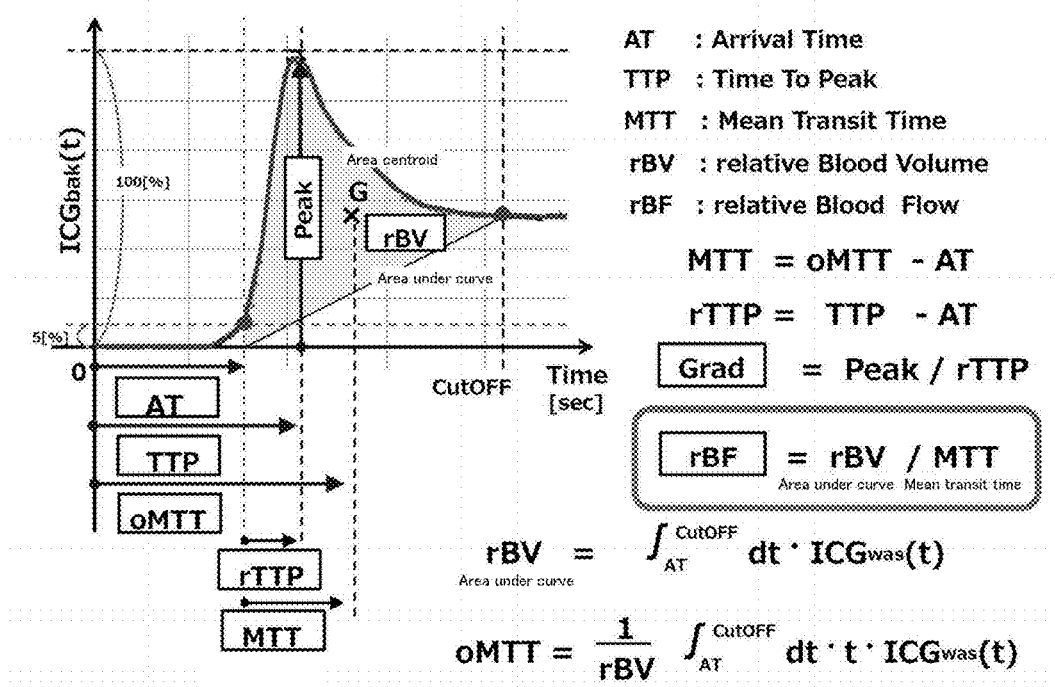
[FIG. 6]
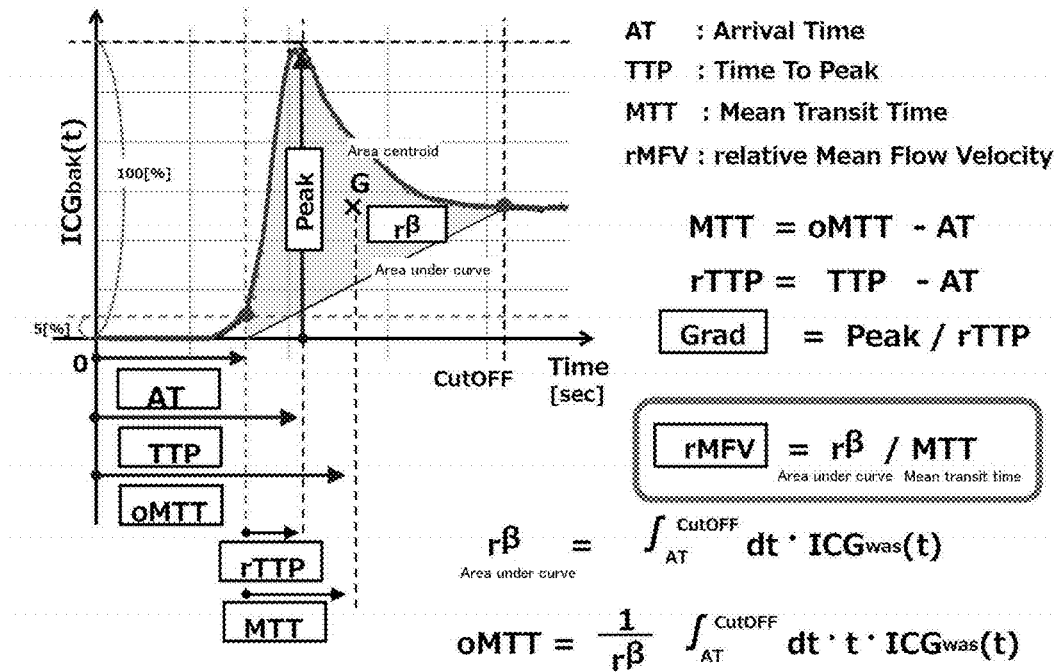

[FIG. 7]
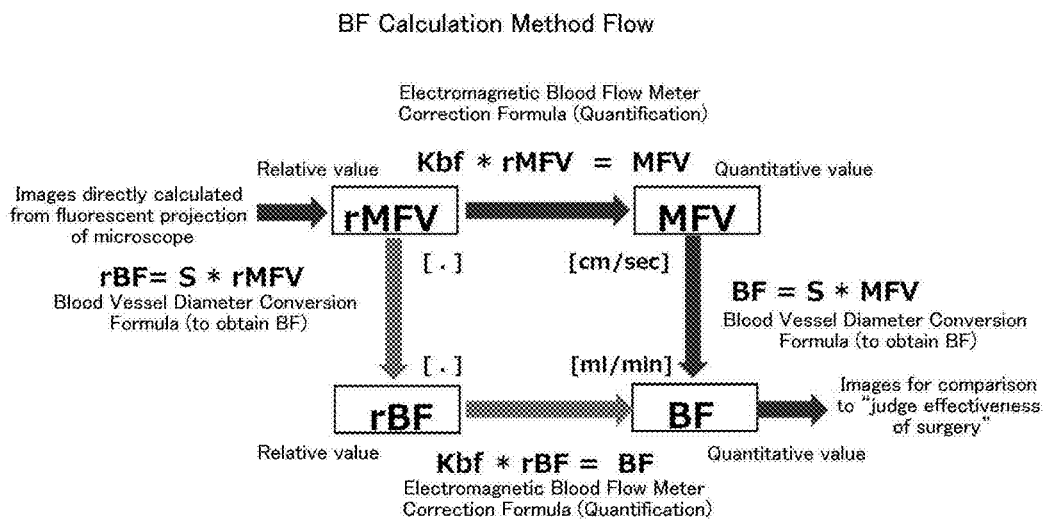
[FIG. 8]
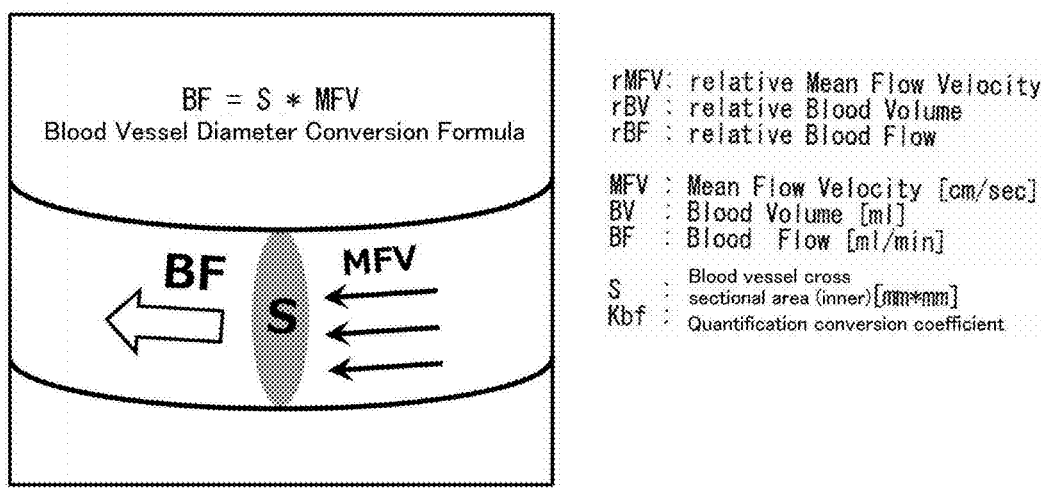

[FIG. 9]

MFV = Kbf * rMFV  : Electromagnetic Blood Flow Meter Correction Formula

BF = S * MFV  : Blood Vessel Diameter Conversion Formula

BF = Kbf * S * rMFV  : Exact formula for BF

[FIG. 10]

MFV = Kbf * rMFV  : Electromagnetic Blood Flow Meter Correction Formula

S ≒ S  : Approximate formula when assuming S is a constant value

BF ≒ Kbf * S * rMFV  : Approximate formula for BF

[FIG. 11]

AT (before bypass)     AT (after bypass)

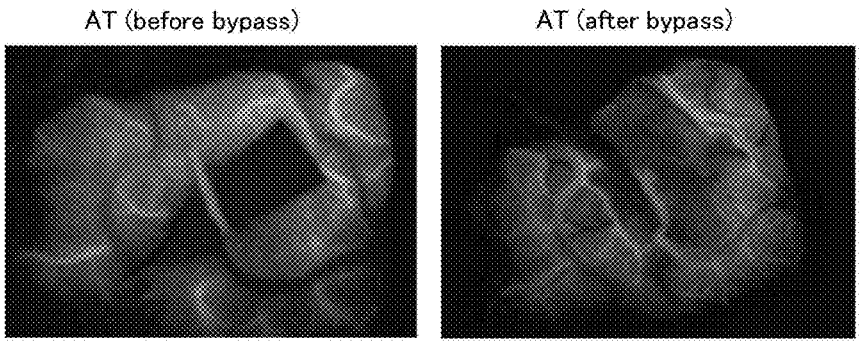

[FIG. 12]
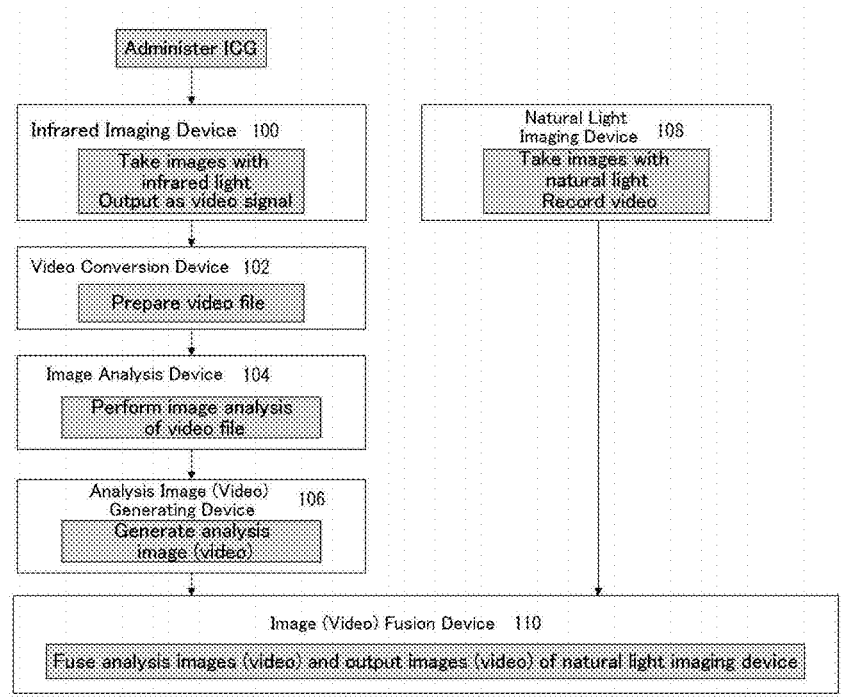
[FIG. 13]
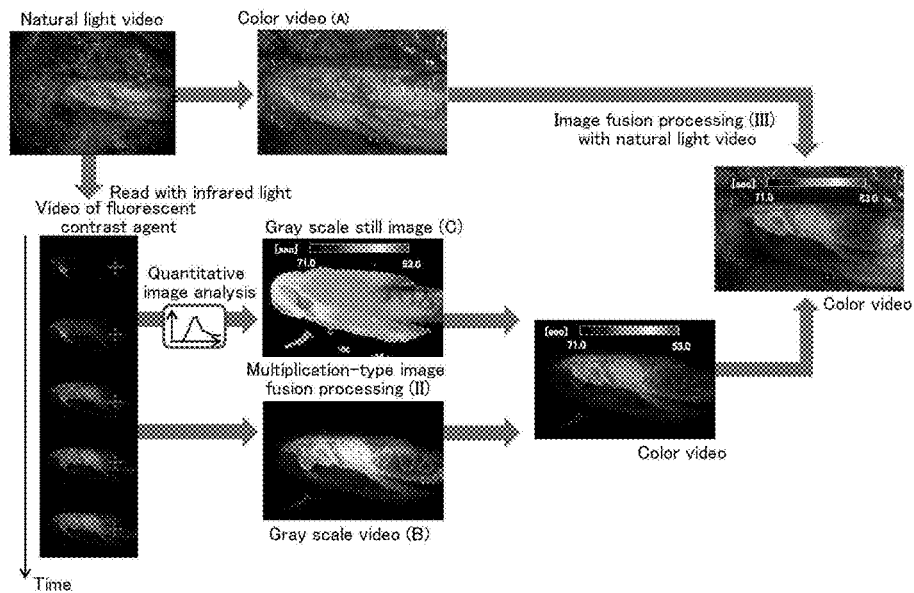

METHOD AND SYSTEM FOR IMAGE PROCESSING OF INTRAVASCULAR HEMODYNAMICS

TECHNICAL FIELD

The present invention relates to a method and system for image processing of intravascular hemodynamics.

BACKGROUND ART

With cerebrovascular diseases such as cerebral aneurysms and moyamoya disease, various tests are performed in order to determine therapeutic results or diagnoses of the diseases. For example, CT (Computed Tomography) tests and MRI (Magnetic Resonance Imaging) tests use tomograms or images reconstructed therefrom, and in angiography, blood vessels are visualized by injecting a contrast agent from a catheter, and consecutively taken images are used to observe the state of the brain parenchyma, the passage of blood vessels, and the flow of blood.

When performing diagnoses for surgical operations on blood vessels, the forms of the organs and blood vessels are observed as images, not only in order to observe ischemia sites and ranges, and to judge the elapsed time from onset, but also to image and numericize the state of blood flow in the blood vessels so as to allow for quantitative and qualitative judgments of the effects of therapeutic results and diagnosis of diseases.

Perfusion imaging is an imaging method wherein, with respect to the blood flow (perfusion) in the capillaries of tissues or the functional vasculature associated therewith, some kind of mark (tracer) is made in the blood flow on the arterial side, and the manner in which the tracer rides the blood flow in passing through the tissues is observed. The method allows for quantitative or semi-quantitative imaging of capillary-level tissue blood flow, and the images taken by such a method are known as perfusion images. Perfusion imaging is a tissue (capillary) analysis method.

Additionally, as parameters for judging the flow of blood, arrival time (AT), time to peak (TTP), blood flow (BF), blood volume (BV) and mean transit time (MTT) are used. For example, when quantitatively evaluating blood flow using a diagnostic image, a time density curve (TDC) indicating the density change over time of an image due to a tracer substance is calculated, and this is analyzed to calculate the aforementioned evaluation value. Furthermore, qualitative images of BF, BV and MTT are prepared on the basis of these evaluation values and TDC analysis, and these qualitative images are used for clinical evaluation.

Tests that allow the state of blood flow to be imaged or numericized include the following.

<Methods Using CT Devices or MRI Devices>

Imaging methods using CT devices are known as CT perfusion, imaging methods using MRI devices are known as MRI perfusion. Perfusion images using CT and MRI are obtained by rapid intravenous injection, as a tracer, of a contrast agent for taking enhanced images of the blood vessels, consecutive imaging of tomograms of the same section, calculation of the TDC representing the concentration change over time at each pixel in the resulting tomograms, and analysis thereof. CT perfusion and MRI perfusion are both tissue (capillary) analysis methods.

CT perfusion involves exposure to X-rays and requires special care when determining quantitative properties in pathologies involving abnormalities in the blood brain barrier, but allows measurements to be taken simply using a standard CT device and analysis software. On the other hand, MRI perfusion has the drawbacks of being inapplicable to patients who have undergone surgery to implant magnetic materials into the body, and involving difficulties in obtaining quantitative data due to linearity not being ensured between the contrast agent concentration and the signal strength. Additionally, neither CT perfusion nor MRI perfusion can be used on patients having allergies to the contrast agent, since the tracer cannot be intravenously injected.

<Methods Using Xe CT>

Methods using non-radioactive Xe (xenon) gas as the tracer make use of the fact that, when Xe gas is inhaled and tomograms are taken by a CT device over time, the Xe spreads to the brain tissue, and the tissue concentration in the CT image (CT value) lightly rises. This increase in the CT value over time is used to calculate the TDC and form an image of the state of blood flow.

Xe gas has stimulatory and narcotic effects and is therefore difficult to use, requires a closed-circuit apparatus for supplying the gas, and also requires care due to X-ray exposure.

<Methods Using SPECT Devices or PET Devices>

Methods using chemicals containing radioisotope elements (hereinafter referred to as RI chemicals) as the tracer, wherein a RI chemical is injected into a peripheral artery or inhaled, and the bodily distribution of the RI chemical over time is measured from outside the body using a SPECT (Single Photon Emission Computed Tomography) device or a PET (Positron Emission Tomography) device to calculate the TDC, and thereby form images of the state of blood flow.

Tests using PET provide the best quantitative performance among currently usable perfusion imaging methods, and they have the advantage of enabling the oxygen intake and energy metabolism to be simultaneously measured. However, since SPECT and PET imaging both involve handling RI chemicals, they require nuclear medical equipment and involve frequent exposure due to testing.

<Methods Using Angiography>

These are methods wherein a catheter is guided to the target blood vessel from the groin, elbow or wrist, a contrast agent is injected into the blood vessel and subjected to X-ray fluoroscopy in order to observe the passage of the blood vessel and constricted sites, and these techniques can be used simultaneously with treatment. The imaging is performed by digital subtraction angiography (DSA), and they allow high-contrast observation of only blood vessels injected with contrast agent. By setting an ROI in a blood vessel to be evaluated in a taken DSA image and analyzing the TDC of a blood vessel (contrast agent) present in the set ROI, the state of blood flow can be imaged.

While angiography allows the effects after intravenous surgery to be easily judged, there is exposure to X-rays, and furthermore, patients who are allergic to the contrast agent cannot be tested. Additionally, since a catheter is directly inserted into the blood vessel, the testing room and testing equipment must have a level of cleanliness on the order of that in an operating room. Additionally, after the operation, several hours of absolute rest are required for hemostasis, so the test basically requires hospitalization.

The diagnoses of vascular diseases are performed not only to image the state of blood flow, but also to quantitatively and qualitatively numericize the state of blood flow and the blood flow rate. This information can be obtained by a method of calculation by analyzing a chronological concentration change graph of the aforementioned images, or by a method using Doppler ultrasound making use of ultrasonic waves, or a blood flow measuring device using an electromagnetic blood flow meter.

<Methods Using Doppler Ultrasound>

By using color Doppler imaging in an ultrasonic analyzer, the hemodynamics in the living body can be colored in real-time, enabling the state of blood flow to be superimposed on a B-mode image which is a two-dimensional tomogram. Color Doppler imaging is a technology that makes use of changes in the frequency of reflected acoustic waves due to the Doppler effect on ultrasonic waves, so as to judge whether or not a target object (blood) is approaching or receding from the probe, and to thereby form images.

Since ultrasonic probe chips are large, they cannot evaluate small blood vessels, and blood flow measurements are also impossible if the probe size differs from the blood vessel diameter, but they allow simple testing without restrictions on location, allow observation from multiple directions, and enable observations to be made in real-time.

<Methods Using Electromagnetic Blood Flow Meters>

These methods are based on Fleming's Law wherein an electromotive force is generated when a conductor is moved in a magnetic field. Blood flow is regarded as electric current, and the generation of an electromotive force in the direction perpendicular to both blood flow and the magnetic field is used to measure the instantaneous blood flow, the mean blood flow and the single stroke volume.

Methods using electromagnetic blood flow meters can be used in blood flow measurements during surgery, and can provide real-time measurement results. However, electromagnetic blood flow meters require the probe to be directly mounted on a blood vessel, so measurements cannot be taken without exposing the blood vessel of interest.

Furthermore, evaluations of blood flow can also be made by observing the flow of blood itself.

<Methods Using Intraoperative Fluorescence Angiography>

These methods evaluate blood flow by taking video, using the near-infrared light from a surgical microscope, of fluorescent light in the near-infrared region that is excited from a fluorescent vascular contrast agent that has been intravenously administered as a tracer.

While they are capable of revealing the state of fluorescent vascular contrast agent in blood vessels (presence or absence of blood flow), they are not capable of analyzing small signal changes such as the state of blood flow and blood flow rate. While the imaging requires video imaging of the blood vessel of interest in the near-infrared light from a surgical microscope device, the state of blood flow during the operation can be confirmed in real-time.

As mentioned above, the evaluation of blood flow in vascular diseases involves various types of tests and measurement methods, but at the site of clinical operations, the optimal testing and measurement methods are considered and used in accordance with the patient pathology, application and diagnostic timing. For example, when evaluating the state of blood flow after aneurysm clipping, the blood flow is evaluated in real-time during the operation. In this case, tests requiring dedicated equipment that is not provided in the operating room, such as CT, MRI and angiography, cannot be used, and blood flow evaluations making use of electromagnetic blood flow meters or intraoperative fluorescence angiography are chosen.

Furthermore, the possibility of using a testing or measuring method also depends on the type of information that can be obtained by the device used. For example, while electromagnetic blood flow meters can be used to measure instantaneous blood flow, mean blood flow and single stroke volume, the outputted data are numerical data (graphs), and while intraoperative fluorescence angiography allows visual estimation of AT and TTP images, the preparation of BV, BF, MTT data and blood flow evaluation images including such information is impossible. For this reason, an operator must evaluate an operation by appropriately choosing devices capable of obtaining information necessary to make the evaluations after an operation, based also on the data measurable thereby. In other words, for example, when wishing to obtain BV, BF or MTT values and blood flow evaluation images, CT perfusion images must be taken several days after surgery when the patient's condition has stabilized, and the taken images must further be analyzed. In other words, it is difficult to obtain BV, BF and MTT values, and blood flow evaluation images, in real-time during an operation.

For example, Patent Document 1 discloses a method of evaluating the patency of a blood vessel that has been subjected to a bypass graft operation, using a fluorescence imaging agent that emits radiation at specific wavelengths.

PRIOR ART DOCUMENTS

Patent Documents

Patent Document 1: JP 2011-147797 A

SUMMARY OF INVENTION

However, with the conventional art, it was very difficult to estimate the desired information such as BV (Blood Volume), BF (Blood Flow) and MTT (Mean Transit Time) from intraoperative fluorescence angiography.

The present invention offers an analysis technique relating to video data of a fluorescent contrast agent taken by a microscope during an operation, and has the purpose of offering a method and system that applies perfusion analysis methods capable of estimating information such as BV, BF and MTT to fluorescent contrast agent analysis, enabling information such as BV, BF and MTT as well as vascular wall thickness to be estimated even by fluorescent contrast agent analysis.

The method for image processing of intravascular hemodynamics according to the present invention is characterized by shooting video using infrared light, wherein the object of shooting is a portion of a blood vessel injected with a standard amount of a fluorescent contrast agent; performing image analysis of a shape of a chronological change curve of intensity values of image outputs from the video shooting; and calculating relative data for blood volume and blood flow based on results of the image analysis.

According to one embodiment of the present invention, quantitative data for the blood volume or blood flow are calculated instead of the relative data.

According to one embodiment of the present invention, blood volume is measured using an electromagnetic blood flow meter, wherein the object of measurement is the portion of the blood vessel; and quantitative data for blood volume or blood flow are calculated based on results of these measurements and the relative data.

According to one embodiment of the present invention, an analysis image is generated from the quantitative data for the blood volume or blood flow. Additionally, an analysis video is generated instead of the analysis image.

According to one embodiment of the present invention, the fluorescent contrast agent is indocyanin green or fluorescein.

According to one embodiment of the present invention, video of the portion of the blood vessel is shot using natural light, and the output images of the video shot using natural light are fused with the output images of video shot using infrared light.

The system for image processing of intravascular hemodynamics according to the present invention is characterized by comprising an infrared imaging device for shooting video images, using natural light, of a portion of a blood vessel injected with a standard amount of a fluorescent contrast agent; and an image analysis device for performing image analysis of a shape of a chronological change curve of intensity values of image outputs shot by the imaging device, and calculating relative data for blood volume or blood flow based on results of the image analysis.

According to one embodiment of the present invention, the image analysis device comprises an image analysis device that calculates quantitative data instead of relative data.

According to one embodiment of the present invention, the system further comprises an analysis image generating device for generating analysis images from the quantitative data for blood volume or blood flow.

According to one embodiment of the present invention, the system further comprises a natural light imaging device for shooting video images of the portion of the blood vessels using natural light; and an image fusion device for fusing the output images of the natural light imaging device and analysis images generated by the analysis image generating device.

The method and system for image processing of intravascular hemodynamics according to the present invention is capable of estimating information such as BV, BF, MTT, and vascular wall thickness.

BRIEF DESCRIPTION OF DRAWINGS

FIG. 1 A flow diagram of a method according to a first embodiment.

FIG. 2 A diagram showing an example of a system configuration.

FIG. 3 A diagram explaining the definitions of output parameter images in the image analysis of the first embodiment.

FIG. 4 A diagram explaining the ROI preparation position.

FIG. 5 A diagram explaining the definitions of output parameter images in the image analysis of the first embodiment.

FIG. 6 A diagram explaining the definitions of output parameter images in the image analysis of the second embodiment.

FIG. 7 A flow diagram explaining the calculation method of BF.

FIG. 8 A diagram explaining the relationship between BF and blood vessel cross-sectional area.

FIG. 9 A diagram explaining the calculation method of BF in the second embodiment.

FIG. 10 A diagram explaining the calculation method of BF in the third embodiment.

FIG. 11 A diagram showing the change in analysis images before and after bypass surgery.

FIG. 12 A flow diagram of a method including an image fusion process.

FIG. 13 A diagram showing the procedure for an image fusion process.

EMBODIMENTS OF THE INVENTION

Herebelow, embodiments of the method and system for image processing of intravascular hemodynamics according to the present invention will be explained. As the present embodiment, an example of a method of diagnosis by calculating BV and BF quantitative images in an operating room during cerebrovascular bypass surgery will be explained.

It should be evident that the present invention is not limited to the following embodiments.

In the following embodiments, the terminology and abbreviations (analysis output image names) correspond as indicated below.

AT: Arrival Time [sec]
TTP: Time To Peak [sec]
MTT: Mean Transit Time [sec]
MFV: Mean Flow Velocity [cm/sec]
BV: Blood Volume [ml]
BF: Blood Flow [ml/min]
rMFV: relative Mean Flow Velocity
rBV: relative Blood Volume
rBF: relative Blood Flow
rTTP: relative Time to Peak (equal to TTP AT)
eBF: electromagnetic blood flow meter-measured Blood Flow [ml/min]
Peak: peak amplitude image
Kbf: quantification conversion coefficient
S: vascular cross-sectional area (inner) [mm*mm]
oMTT: absolute time of area centroid [sec] (equal to MTT+AT)
Fusion: image fusion
ROI: Region of Interest
ICG: Indocyanin green
FITC: Fluorescein isothiocyanate In the present embodiment, image output refers to output by images, video, or images extracted from frames of video.

First Embodiment

First, the configuration of the system for image processing of intravascular hemodynamics according to the first embodiment will be explained. The system according to the present embodiment, as shown in FIG. 1, comprises an infrared imaging device 100 for taking video of blood vessels using infrared light, a video conversion device 102 for converting the video signals outputted from the infrared imaging device 100 and preparing a video file, an image analysis device 104 for analyzing the video file converted by the video conversion device 102 and calculating relative data for blood volume or blood flow based on the image analysis results, and an analysis image generating device 106 for generating an analysis image from quantitative data for the blood volume or blood flow obtained by the image analysis device 104.

These devices can, for example, be provided within a single personal computer.

Alternatively, they may be separate devices. Alternatively, some or all of the functions could be installed in a personal computer, or in measuring equipment, a display device or an analysis device in the form of software.

FIG. 2 shows an example of the configuration of a system according to the present embodiment. FIG. 2 describes an example of the configuration of the invention according to the present embodiment in microsurgery (surgery performed using a microscope).

The procedure for carrying out the method according to the present embodiment is as described below.

[Administration of Fluorescent Contrast Agent]

Indocyanin green is administered as a fluorescent contrast agent. The administration is performed transvenously or transarterially. Ex.) 25 mg of indocyanin green is diluted to 10 ml and administered 2 ml at a time.

As the fluorescent contrast agent, indocyanin green (ICG) or fluorescein isothiocyanate (FITC) may be used. ICG polymerizes with a-lipoproteins in blood to emit monochromatic fluorescent light in response to infrared light. This phenomenon is used in the field of ophthalmology for application to fundus fluorescent angiography. FITC is a fluorescent pigment that emits green light when exposed to ultraviolet rays.

Aside from the above-described fluorescent contrast agents, other chemical agents may be appropriately used as long as they emit light of specific wavelengths when illuminated by light of specific wavelengths.

[Measurement of Quantitative BF Value Using Electromagnetic Blood Flow Meter]

An electromagnetic blood flow meter is used to measure the quantitative blood flow value at a single specific blood vessel position. The actual measurement operations using an electromagnetic blood flow meter are performed by sandwiching a blood vessel structure including a bypass graft in between electromagnetic blood flow meter probes.

[Video Imaging]

Video is taken with the infrared imaging device 100. As the infrared imaging device 100, a common surgical microscope capable of infrared imaging may be used.

[Video File Conversion]

Analog (composite) video signals taken with the infrared imaging device 100 are analog-digital converted using a video capture device in the video conversion device 102. The digital video signals are loaded as video files into a local disk using a personal computer. The video files may be common video files such as MPEG or MOV.

[Quantitative Analysis of Video Files]

In the image analysis device 104, the image output of video images is analyzed by the following procedure.

In this case, the quantitative MTT data and relative rBV and rBF data are calculated by carrying out a first moment calculation procedure of perfusion analysis using a fluorescent angiography chemical during surgery, while simultaneously measuring the quantitative BF value using an electromagnetic blood flow meter on a single specific blood vessel which is visible in the surgical field of vision before vascular surgery.

First, a single point (single pixel) in a blood vessel in an image is monitored over the passage of time. As a result, information on the change in the intensity value at that single point (single pixel) in the blood vessel can be obtained. In this case, the information on the change in intensity value can be obtained for just a single pixel, or the information may be the mean value for the intensity values of a plurality of pixels.

By analyzing the chronological intensity value change curve, the state of passage of a clump of the ICG agent through the blood vessel can be quantitatively examined. The quantitative analysis shown in FIG. 3 is performed for all pixels in the video image. AT, TTP and MTT, for which the analysis results are calculated in units of time (X axis), are determined as quantitative image data. rBV and rBF for which the analysis results are calculated from the integral of the intensity value (Y axis) are determined as relative image data.

While observing video data of the fluorescent contrast agent as a guide image, an ROI is prepared at the same blood vessel position as the specific blood vessel position that was measured with the electromagnetic blood flow meter (FIG. 4). Next, an ROI statistical procedure is performed on the rBF image. The mean relative blood flow calculated by the ROI statistical procedure is defined as rBF (ROI). The conversion coefficient Kbf between eBF (ROI) and rBF (ROI) is calculated.

$$eBF(ROI)=Kbf*rBF(ROI)$$

Here, ROI refers to a Region of Interest. ROI preparation is a process of preparing a region of interest by surrounding the region of interest in an image being observed with a two-dimensional closed curve. ROI statistics refer to image processing to calculate the mean image value per unit pixel inside an ROI shape.

The quantification conversion formula that is established for a specific blood vessel position (ROI):

$$eBF(ROI)=Kbf*rBF(ROI)$$

is assumed to be a quantification conversion formula that applies to all positions in the image space.

In other words, as shown in the following formula, conversion to the quantitative BF is possible by multiplication with the entire relative rBF image calculated by the first moment calculation procedure in perfusion analysis.

$$BF=Kbf*rBF$$

Due to the relationships established by first moment calculation in perfusion analysis:

$$rBF=rBF/MTT, BF=BV/MTT$$

and the quantification conversion formula for converting relative rBF images to quantitative BF images:

$$BF=Kbf*rBF$$

the following quantification conversion formula for converting relative rBV images to quantitative BV images is established.

$$BV=Kbf*rBV$$

The above-described parameters are related as shown below.

rBF=rBV/MTT      relative relationship

BF=BV/MTT      quantitative relationship quantification conversion formula established at specific blood vessel position (ROI)

quantification conversion formula between rBF and BF established for entire image quantification conversion formula between rBV and BV established for entire image An output parameter image for image analysis can be extracted from the shape of the chronological intensity value change curve obtained from the information on the change in intensity value at one point in the blood vessel as shown in FIG. 5, and the relationship between the parameters is a relationship as shown in FIG. 5.

Examples of analysis images before and after bypass surgery are shown in FIG. 11. This example shows that, after bypass surgery, the AT became shorter (the blood flow became faster), and the dark area in the center of the image became larger.

Quantitative intraoperative fluorescence angiography depends on the timing of the intravenous injection of the fluorescent contrast agent, and it is difficult to obtain stable results. By determining the integral value from the chronological intensity value change curve and determining the centroid of the area, stable BF, BV and MTT values that do not depend on the timing of the injection can be determined Additionally, by referring to the graft blood flow due to the electromagnetic blood flow meter, a more precise BF can be calculated in consideration of the dosage of the graft blood vessel diameter and the amount of the fluorescent contrast agent administered. In accordance with need, tests can be repeated at standard timings by injecting a fluorescent contrast agent into the carotid artery.

As described above, the method according to the present embodiment allows the state of the blood vessels before or after vascular surgery to be diagnosed by measuring quantitative BF values of specific blood vessels using an electromagnetic blood flow meter, and it can provide the information in a particularly visually recognizable form.

Additionally, with a first moment method in perfusion analysis such as CT perfusion and MRI perfusion used as the analysis method for the tissues (capillaries), the area under the curve is defined as relative rBV, so the relative rBV image can be easily determined for each pixel. Additionally, when defining the AT time as the origin zero [sec], the time of the area centroid is defined as the quantitative MTT. The quantitative MTT can also be easily determined for each pixel.

In conventional perfusion analysis methods, it is known that the equation rBF=rBV/MTT is established between the relative rBV and the relative rBF. While the quantitative BV and BF images cannot be estimated using only the first moment method of conventional perfusion analysis, according to the method of the present embodiment, the relative rBF image can be easily determined from the relative rBV image and the quantitative MTT image for each pixel by using the equation rBF=rBV/MTT.

Second Embodiment

In the method of the second embodiment, the calculation technique for the "quantitative analysis of the video file" differs from that of the first embodiment, but the system configuration and other steps in the method are the same as in the first embodiment.

Herebelow, the calculation method will be explained for the case wherein the perfusion imaging method (first moment method) for CT perfusion and MRI perfusion, which are tissue (capillary) analysis methods, are used in the blood vessel analysis method using intraoperative fluorescent angiography data (using a microscope camera).

In tissue (capillary) analysis using perfusion imaging (first moment method), when the AT time is defined as the origin zero [sec], the time at the area centroid is defined as the quantitative MTT and the area under the curve is defined as the relative rBV. The following relationship is established between the relative rBV, the relative rBF and the quantitative MTT.

$$rBF=rBV/MTT$$

The electromagnetic blood flow meter correction formula for tissue (capillary) analysis will be considered. The relative rBF can be quantitatively converted to a BF [ml/min] image by measuring the quantitative BF [ml/min] at a specific blood vessel position using an electromagnetic blood flow meter.

$$BF\ [ml/min]=Kd*rBF\quad\text{magnetic blood flow meter correction formula}$$

Here, BF [ml/min] refers to the quantitative blood flow that is "flowing per unit tissue".

Tissue (capillary) analysis allows the BF [ml/min] and the BV [ml/min] to be directly calculated. The concept of "flowing per unit tissue" can be predicted to be inappropriate for blood vessel analysis. In blood vessel analysis, the BF [ml/min] and BV [ml] flowing in a single blood vessel must be calculated.

The exact solution when applying tissue (capillary) analysis using perfusion imaging (first moment method) to blood vessel analysis will be studied. In blood vessel analysis, when the AT time is defined as the origin zero [sec], the time at the area centroid is defined as the quantitative MTT. This relationship is no different from that in tissue (capillary) analysis.

The quantitative MTT is a calculated quantity that can be defined by using the same concepts for both tissue analysis and capillary analysis. The area under the curve is defined as rβ. The following relationship is established between the relative rβ, the quantitative MTT and the rMFV (Mean Flow Velocity).

$$rMFV=r\beta/MTT$$

In this embodiment, the aforementioned rBF in FIG. 3 corresponds to rβ.

An explanation of the above-described relationship is shown in FIG. 6. This relationship was able to be derived from data analysis of phantom tests performed by changing the blood vessel diameter. As a result of the phantom tests, rβ/MTT was not proportional to rBF. The tests came to the conclusion that "rβ/MTT" is proportional to "rBF/S".

The electromagnetic blood flow meter correction formula for the blood vessel analysis will be contemplated. The relative rMFV can be quantitatively converted to MFV [cm/sec] by measuring the quantitative MFV [cm/sec] at a specific blood vessel position using an electromagnetic blood flow meter.

$$MFV\ [cm/sec]=Kbf*rMFV\quad\text{electromagnetic blood flow correction meter}$$

MFV [cm/sec] is the mean blood flow velocity that is "flowing per unit space". Here, the space in "per unit space" is considered to refer to both blood vessels and tissues (capillaries).

The blood vessel diameter conversion formula for blood vessel conversion will be considered. The quantitative value to be finally calculated is BF [ml/min], so a method of calculating quantitative BF will be considered. The following blood vessel diameter conversion formula is established between the quantitative MFV and the quantitative BF.

$$BF\ [ml/min]=S\ [mm*mm]*MFV\quad\text{blood vessel diameter conversion formula}$$

A summary of the BF calculation process is shown in the flow diagram of FIG. 7.

Additionally, as shown in FIG. 8, S is defined as the inner blood vessel cross-sectional area at a certain blood vessel position.

This blood vessel diameter conversion formula means that the quantitative BF can be calculated if the inner blood vessel cross-sectional area S can be measured at the position of each blood vessel. The fact that the inner blood vessel cross-sectional area S is not a single value is important. The thickness (blood vessel cross sectional area) of a blood vessel differs for each blood vessel. Additionally, when considered strictly, the thickness (blood vessel cross sectional area) of a blood vessel will differ even in a single blood vessel if the position is different. These differences mean that the inner blood vessel cross sectional area S is given exactly by the image.

When using perfusion imaging (first moment method) blood vessel analysis, the directly obtained physical quantity is the relative rMFV. From this relative rMFV, the quantitative BF can be calculated by using the electromagnetic blood flow meter correction formula (MFV=Kbf*rMFV) and the blood vessel diameter conversion formula (BF=S*MFV) (FIG. 9).

The method of the second embodiment enables a more exact BF value to be calculated.

Third Embodiment

With the method of the third embodiment, the formula for calculating BF differs from the second embodiment, but the other steps relating to the system configuration and method are the same as in the first embodiment.

In order to exactly calculate BF, the inner blood vessel cross sectional area S [mm*mm] must be exactly measured. However, it is difficult to exactly measure the inner blood vessel cross sectional area S [mm*mm]

In the step of performing electromagnetic blood flow meter correction, the blood flow velocity (blood flow) is measured at a certain single blood vessel position. The blood vessel diameter R [mm] at this single location can be measured. The inner blood vessel cross sectional area S is determined from the measured blood vessel diameter R [mm] As the first approximation, the inner blood vessel cross sectional area S is approximated as being the same within the same single blood vessel measured by the electromagnetic blood flow meter.

The inner blood vessel cross sectional area S of other blood vessels not measured by the electromagnetic blood flow meter are also approximated. Due to this approximation, the inner blood vessel cross sectional area: S image, for which exact measurement was difficult, can be treated as a constant.

Due to the method of the third embodiment, the perfusion image (first moment) blood vessel analysis can be calculated by approximation.

Fourth Embodiment

As a fourth embodiment, a method that allows analysis similar to the first to third embodiments to be performed without performing electromagnetic blood flow meter measurements, by defining the operating conditions, will be explained. The fourth embodiment is the same as the above-described first to third embodiments, other than the fact that the operating conditions are defined without performing electromagnetic blood flow meter measurements.

It is not easy to perform electromagnetic blood flow meter measurements every time. The measurement operations for electromagnetic blood flow measurements include the risk of damaging the blood vessel structure, and under current conditions, should be avoided as much as possible. The quantitative BV and BF images can be approximately calculated by matching the operating conditions, even without using an electromagnetic blood flow meter. In this case, the operating conditions include the sensitivity of the microscope camera, the magnification of the microscope camera, the working distance of the microscope camera, the angle of the microscope camera, and the amount of the fluorescent contrast agent administered.

The "working distance" refers to the distance from the tip of the objective lens of the microscope camera to the object being imaged, on which the focal point is trained. The "angle" refers to the angle at which the microscope camera is viewing the object being imaged.

The amount of the fluorescent contrast agent administered refers to the amount of chemical injected when injecting the fluorescent contrast agent (ICG; FITC) from a vein in the arm. Generally, the fluorescent contrast agent is diluted to make it easier to inject. This means that the state of dilution is made the same and that the same amount of injected chemical is injected after dilution. The specific conditions for matching the operating conditions can be determined by each organization, for example, by the hospital.

In the method according to the fourth embodiment, the quantitative BV and BF images can be approximately calculated by matching the operating conditions, without using an electromagnetic blood flow meter or technology that allows the quantitative BV and BF images to be calculated by using an electromagnetic blood flow meter. For this reason, there are specific effects such as predictions of the blood flow that can be supplied to tissues by a bypass graft, and the long-term patency of a bypass.

[Measurement of Blood Vessel Wall Thickness]

In cerebral aneurysms and carotid artery stenotic lesions, thickness information can provide information on the risks involved in surgical operations such as the tear susceptibility of arterial aneurysms and release of thrombi from stenotic lesions.

ICG is capable of viewing to depths of 10 mm due to its fluorescence frequency. Blood vessel walls are about 0.1 to 10 mm thick, and the properties of blood vessel walls are important during surgery. Since the ICG intensity changes depending on the blood vessel wall thickness, the wall thickness can be estimated by holding constant the amount administered, the microscope camera sensitivity, the distance to the object being observed, and the magnification.

FITC can view down to depths of 5 mm due to its fluorescence frequency. It is capable of observing blood vessel lesions having relatively thin blood vessel walls, and the patency of bypasses.

The present method has the purpose of determining the blood flow (BF), blood volume (BV) and mean transit time (MTT) not only of brain tissue, but also of blood vessels themselves, as well as the thickness of blood vessel walls from the signal intensity.

[Image Fusion Process]

With just the above-mentioned output parameter image data from the results of fluorescent contrast agent analysis, the relationships between the anatomical positions such as arteries/veins and cerebral sulci are unclear. The relationships between the anatomical positions can be understood by performing image superimposition (image fusion) of output parameter image data of fluorescent contrast agent analysis results onto anatomical image (video) data.

While image fusion is a tissue (capillary) analysis method, it requires a blood vessel analysis method. The results of the above-described image processing of intravascular hemodynamics can be used. The system used for the intravascular hemodynamics image processing method including an image fusion process has the configuration shown in FIG. 12.

In image processing of intravascular hemodynamics including an image fusion process, imaging is performed with a natural light imaging device 108 as well as imaging with an infrared imaging device 100. In this case, imaging is performed by natural light, and image or video data are recorded.

An image fusion device 110, with the natural light imaging device 108 that takes video of a portion of a blood vessel by natural light, fuses the output images from the natural light imaging device 108 and the analysis (video) images generated by the analysis image (video) generating device 106.

In image fusion, the following types of image (video) data (A), (B) and (C) are used.
(A) M-frame natural light video data (color images)
(B) N-frame fluorescent contrast agent video data (gray scale images)
(C) Still image data of analysis results (color scale images) [sometimes including plural data such as BF, BV and MTT]

In this case, the (gray scale images) refer to value-type images (used primarily in MRI and CT for medical images) in which the display colors are assigned by referring to a gray scale color table.

The (color scale images) refer to value-type images (used primarily in nuclear medicine for medical images) in which the display colors are assigned by referring to color tables of rainbow colors etc.

The (color images) refer to images in which the colors are fixed as in photographs.

In this case, N-frame video data refers to images consisting of an animation of N frames in the time axis direction. Still image data refers to a single image like a photograph.

The fluorescent contrast agent analysis according to the art of the above-described Embodiment 1 or 2 is a process of deriving (C) from (B). The important points are that (A) is not used in processing of only fluorescent contrast agent analysis, and that (B) and (C) have the same positional relationship because the still image (C) is prepared from video (B). Regarding the image fusion process for (B) and (C), since they are at the same position, their positional relationship is always aligned.

Whether (A) has the same positional relationship as (B) and (C) differs depending on the equipment used. There are devices in which the shooting positions of the natural light video and the infrared light video differ and devices in which the positions are the same. Additionally, the number M of animation frames of the natural light video and the number N of animation frames of the fluorescent contrast agent video generally differ. Additionally, whether the time of shooting of the natural light video and the time of shooting of the fluorescent contrast agent video are the same also differs depending on the microscopy equipment. Whether or not they are shot at the same time is not an essential condition for the image fusion process.

For the present embodiment, the next three types of image fusion process will be explained.

(I) Image fusion process I (multiplication type image fusion process): Image fusion process I wherein image fusion still image data (color images) are prepared by image fusion processing of peak still image data (gray scale images) calculated from fluorescent contrast agent video data and output parameter still image data (gray scale images) from (C) image analysis.

With this process, a (single color image) is prepared by combining a (single gray scale image) and a (single color scale image).

(II) Image fusion process II (multiplication type image fusion process): Image fusion process II wherein image fusion video data (color image) is prepared by image fusion processing of (B) fluorescent contrast agent video data (gray scale image) and (C) image analysis output parameter still image data (color scale image).

With this process, (N-frame color images) are prepared by combining (N-frame gray scale images) and a (single color scale image).

(III) Image fusion process III (natural light video and image fusion process): Image fusion process III wherein image fusion video data (color images) are prepared by image fusion processing of image fusion video data (color images) prepared by image fusion processing and (A) natural light video data (color images) or (A) natural light still image data (color images).

With this process, an (N-frame color image) is prepared by combining an (N-frame color image) and an (M-frame or single color image).

FIG. 13 shows an example of a processing procedure for image superimposition processing (image fusion processing). This processing procedure involves performing image fusion process II and image fusion process III, and preparing an (N-frame color image) from a combination of an (N-frame color image) and an (M-frame or single color image).

Image fusion process I and image fusion process II both involve performing the same multiplication-type image fusion process. The difference between image fusion process I and image fusion process II is that, in (I), there is one (gray scale image), whereas in (II), there are N frames of (gray scale images). The (C) image analysis output parameter still image data (color scale image) is also a single frame.

In image fusion process I, just one multiplication-type image fusion process is performed. In image fusion process II, the process is performed N times while changing the fluorescent contrast agent video data (gray scale images). As for the resulting images for the image fusion processes, image fusion process I results in a still image, and image fusion process II results in video.

The details of the multiplication-type image fusion processes that are commonly used in both image fusion process I and image fusion process II will now be explained. The advantage of multiplication-type image fusion processes is that the color of both gray scale images and color images can be reliably reproduced.

Herebelow, the specific processing procedure for a multiplication-type image fusion process will be explained for a single gray scale image and a single color scale image. First, the fact that addition-type image fusion processes are not optimal will be explained.

Addition-type image fusion processes use calculations based on the following basic formulas.
Color of color scale image 1=(Red1, Green1, Blue1)
Color of color scale image 2=(Red2, Green2, Blue2)
Color of image after image fusion process=(FusionRed, FusionGreen, FusionBlue)
$\alpha$: synthesis ratio which is a value represented by a number between 0.0 and 1.0.

$$FusionRed = \alpha * Red2 + (1.0 - \alpha) * Red1$$

$$FusionGreen = \alpha * Green2 + (1.0 - \alpha) * Green1$$

$$FusionBlue = \alpha * Blue2 + (1.0 - \alpha) * Blue1$$

Since the addition-type image fusion process formula adds the colors of the two images, it is referred to as an addition-type image fusion processing formula.

In addition-type image fusion, in the case of a single gray scale image and a single color scale image:

The colors of color scale image 1=(Red1, Green1, Blue1) are replaced by the colors of a gray scale image=(Gray, Gray, Gray).
The colors of color scale image 2=(Red2, Green2, Blue2) are replaced by the colors of a color scale image=(Red, Green, Blue)

$$FusionRed=\alpha*Red+(1.0-\alpha)*Gray$$

$$FusionGreen=\alpha*Green+(1.0-\alpha)*Gray$$

$$FusionBlue=\alpha*Blue+(1.0-a\alpha)*Gray$$

It can be seen that the addition-type image fusion processing formula is not capable of reproducing the colors (Red, Green, Blue) of the color scale image.

In this way, addition-type image fusion processing is a technique that is incapable of reliably reproducing the colors (Red, Green, Blue) in a color scale image. In contrast, the multiplication-type image fusion processing formula multiplies the colors of two images, and is therefore referred to as a multiplication-type image fusion processing formula.

By using a multiplication-type image fusion processing formula, the colors (Red, Green, Blue) of color scale images can be reliably reproduced. The positions where the gray scale image is black can always be made black in the color scale image after fusion processing. The positions where the gray scale image is white can be made the same as the color (Red, Green, Blue) of the gray scale image of the original image in the color scale image after fusion processing.

There are cases in which only a single natural light still image of a specific time is used from among M-frame natural light video data. In cases such as when it becomes complicated to use video, the process can be simplified by using just a single natural light still image.

Embodiments of the present invention have been explained above. A part of the method of the first embodiment may be replaced with the fourth embodiment. Additionally, a part of the method of the first embodiment may be replaced by the second embodiment or the third embodiment. In other words, the above-described embodiments may be combined.

As explained above, in vascular surgical operations, it is very important to keep abreast of the state of blood flow during the operation. The judgment of therapeutic effects of vascular surgery is important, such as whether cerebral blood flow blockage is complete, or whether adequate blood volume is provided to shunt blood vessels. In the inventions according to the embodiments described above, the BF, BV and MTT which could not conventionally be observed by fluorescent contrast agent analysis can be stably observed, and the inventions further can estimate the blood vessel wall thickness by signal intensity changes, and provide anatomical orientation by natural light and fusion. By fusing fluorescent contrast agent analysis results with images shot in natural light, the anatomical positional relationship can also be easily understood.

In particular, it becomes possible to predict the long term patency of grafts and to predict the risk of hyperperfusion including evaluations of blood flow from grafts, to observe the state of blood flow changes on the brain surface, and to detect BV and BF changes caused by brain function reactions. Furthermore, there is a possibility that monochromatic video editing can be applied not only to fluorescent contrast agent analysis, but also to similar analysis of gray scale video, such as normal blood vessel imaging. By quantitatively comparing the state before vascular surgery and the state after vascular surgery using quantitative BV, BF and MTT images, therapeutic effects can be judged immediately after vascular surgery.

In conventional methods, the amount and timing of intravenous injection of the fluorescent contrast agent are important, and since the fluorescent contrast agent is metabolized in the liver, the attenuation history of the intensity of the fluorescent contrast agent will change depending on the liver function. The quantitative BV, BF and MTT images calculated by the invention according to the above-described embodiments are capable of minimizing the effects of differences even if there are differences in the timing of injection of the fluorescent contrast agent. For this reason, the invention provides an analysis method that is effective for judging therapeutic effects.

Additionally, there may be symptoms due to hyperperfusion of blood flow after bypass surgery. In such cases, predictive diagnoses can be made by observing the BV and BF quantitative images after bypass surgery. Since hyperperfusion carries the risk of hemorrhage and convulsions, it is extremely useful to be able to predict these symptoms during the operation. The predictive diagnosis of such symptoms was difficult given only AT and TTP information which was provided by the conventional art, while the invention according to the above-described embodiments is capable of handling such predictions.

Additionally, by using fusion images, it is also possible to predict whether hyperperfusion is likely to occur in a certain area.

While the method and system according to the present invention can be applied to vascular surgery in the fields of neurosurgery, orthopedic surgery and ophthalmic surgery using microscopes during the operation, there is no particular limitation thereto, and they can be applied to various forms of vascular surgery.

DESCRIPTION OF REFERENCE SIGNS

100 Infrared light imaging device
102 Video conversion device
104 Image analysis device
106 Analysis image (video) generation device
108 Natural light imaging device
110 Image (video) fusion device

The invention claimed is:
1. A method for acquisition and processing of intravascular hemodynamics images, comprising:
shooting video of an image space using infrared light, wherein the object of shooting is a portion of a blood vessel injected with a fluorescent contrast agent, and the video is shot through a microscope during surgery;
performing image analysis of image outputs from the video shooting to determine a chronological change curve of intensity values of the image outputs from the video shooting;
measuring a local quantitative blood flow at a region of interest within the image space using a blood flow meter;
calculating relative data for blood volume or relative data for blood flow at the region of interest and at other positions in the image space that differ from the region of interest based on the chronological change curve resulting from the image analysis;
calculating quantitative data for blood volume or quantitative data for blood flow at the other positions in the image space based on the local quantitative blood flow measured at the region of interest and the relative data for blood volume or the relative data for blood flow calculated for the region of interest;

wherein the relative data for blood volume is calculated based on an integral value from the chronological change curve or the relative data for blood flow is calculated based on the integral value from the chronological change curve and a centroid of an area under the chronological change curve.

2. The method for acquisition and processing of intravascular hemodynamics images according to claim 1, wherein the fluorescent contrast agent is indocyanin green.

3. The method for acquisition and processing of intravascular hemodynamics images according to claim 1, wherein the fluorescent contrast agent is fluorescein.

4. The method for acquisition and processing of intravascular hemodynamics images according to claim 1, comprising:

converting the relative data for blood flow to quantitative data using a quantification conversion formula $BF=Kbf*rBF$ or converting the relative data for blood volume to quantitative data using a quantification conversion formula $BV=Kbf*rBV$;

wherein BF represents quantitative blood flow, Kbf represents a quantification conversion coefficient, rBF represents relative blood flow, BV represents quantitative blood volume, and rBV represents relative blood volume.

5. The method for acquisition and processing of intravascular hemodynamics images according to claim 1, wherein the blood flow meter is an electromagnetic blood flow meter, comprising:

converting the relative data for blood flow to quantitative data using an electromagnetic blood flow meter correction formula $MFV=Kbf*rMFV$ and a blood vessel diameter conversion formula $BF=S*MFV$;

wherein MFV represents a mean flow velocity, Kbf represents a quantification conversion coefficient, rMFV represents a relative mean flow velocity, BF represents the quantitative blood flow, and S represents a vascular cross-sectional area.

6. A system for acquisition and processing of intravascular hemodynamics images, comprising:

a surgical microscope;

an infrared imaging device for shooting video images through the surgical microscope, using infrared light, of an image space including a portion of a blood vessel injected with a fluorescent contrast agent; and an image analysis device configured to receive a quantitative blood flow measurement from a blood flow meter arranged at a region of interest within the image space;

wherein the image analysis device is further configured for performing image analysis of image outputs from the video shooting to determine a chronological change curve of intensity values of image outputs shot by the infrared imaging device, and calculating relative data for blood volume or relative data for blood flow at the region of interest and at other positions in the image space that differ from the region of interest based on the chronological change curve resulting from the image analysis, wherein the image analysis device is configured to calculate the relative data for blood volume based on an integral value from the chronological change curve or to calculate the relative data for blood flow based on the integral value from the chronological change curve and a centroid of an area under the chronological change curve;

wherein the image analysis device is further configured to calculate quantitative data for blood volume or quantitative data for blood flow at the other positions in the image space based on the quantitative blood flow measurement from the blood flow meter at the region of interest and the relative data for blood volume or the relative data for blood flow calculated for the region of interest.

* * * * *